_United States Patent_ [19]

Kritzler et al.

[11] 4,059,627
[45] Nov. 22, 1977

[54] CHLORINATED AROMATIC AMINES

[75] Inventors: Helmuth Kritzler, Odenthal; Walter Böhm, Leverkusen; Wolfgang Kiel, Schildgen; Udo Birkenstock, Ratingen, all of Germany

[73] Assignee: Bayer Aktiengesellschaft, Leverkusen, Germany

[21] Appl. No.: 737,645

[22] Filed: Nov. 1, 1976

[30] Foreign Application Priority Data

Nov. 6, 1975 Germany .............................. 2549900

[51] Int. Cl.$^2$ ............................................. C07C 85/11
[52] U.S. Cl. .............................. 260/580; 260/534 R; 260/571; 260/575
[58] Field of Search ................ 260/580, 571, 575, 689

[56] References Cited

U.S. PATENT DOCUMENTS

| | | | |
|---|---|---|---|
| 3,538,161 | 11/1970 | Dovell | 260/576 |
| 3,739,026 | 6/1973 | Wilson | 260/576 |
| 3,920,743 | 11/1975 | Raessler et al. | 260/580 |

_Primary Examiner_—Allen B. Curtis
_Assistant Examiner_—John J. Doll
_Attorney, Agent, or Firm_—Burgess, Dinklage & Sprung

[57] ABSTRACT

An improvement in a process for the preparation of chlorinated aromatic amines by hydrogenation of the corresponding chlorinated nitro-aromatic compounds in the presence of a noble metal catalyst on a carbon support and in the presence of a sulfur compound, the improvement residing in that the sulfur compound is a thio-ether. Preferably the reaction is carried out in a weakly basic medium.

13 Claims, No Drawings

CHLORINATED AROMATIC AMINES

The invention relates to a process for the preparation of chlorinated aromatic amines by selective hydrogenation of chloronitro-aromatic compounds.

As is known, the hydrogenation of chlorinated aromatic nitro compounds is accompanied by a more or less extensive dechlorination, depending on the hydrogenation catalyst used (J. prakt. Chem. 317, Number 2, page 247 (1975). The consequences are a reduction in the yield of the desired halogenated amines and extensive corrosion in the apparatuses as a result of the hydrogen chloride formed. It is an object of the present invention to minimise dechlorination.

Various processes are already known, with the aid of which attempts are made to keep the elimination of chlorine as low as possible. According to these processes, either the hydrogenation catalyst is specially modified or a dehalogenation inhibitor is added to the customary catalyst during the reaction.

The first-mentioned procedure includes, for example, the use of noble metal sulphides (French Patent Specification 1,417,236 and Am. Soc. 87, 2767 (1965)), of sulphided platinum contact catalysts (German Ausleges-chrift (German Patent Specification) 1,959,578) and of sulphited platinum contact catalysts (German Patent Specification 2,105,780) or the use of noble metal catalysts which are treated with sulphoxides and then with hydrazine before they are used (German Auslegeschrift (German Published Specification) 2,150,220).

Processes which comprise separate addition of an inhibitor and a catalyst to the reaction mixture include, for example, the known use of platinum catalysts which are employed with the addition, at the same time, of magnesium hydroxide (British Patent Specification 859,251), of morpholine or piperazine (U.S. Patent Specification 3,546,297) or of triphenyl phosphite (U.S. Patent Specification 3,474,144).

The preparation of the modified catalysts involves high expenditure; this applies in particular in the case of catalysts modified with hydrogen sulphide or substances which form hydrogen sulphide (German Auslegeshcrift (German Published Specification) 1,959,578) and sulphone/hydrazine (German Auslegeschrift (German Published Specification) 2,150,220), since the toxicity of these additives necessitates special precautions during the preparation.

The elimination of chlorine can be only partially prevented by the addition of the known inhibitors. Long reaction times are necessary in order to keep the elimination of chlorine as low as possible with this procedure. This gives rise to an involved reaction procedure and low space/time yields, which are disadvantageous.

The present invention provides a process for the preparation of a chlorinated aromatic amine comprising hydrogenation of the corresponding chlorinated nitro-aromatic compound in the presence of a noble metal catalyst on a carbon support and in the presence of a thio-ether. The process is optionally carried out in a weakly basic medium.

The hydrogenation according to the process of the invention may be illustrated using the hydrogenation of p-chloronitrobenzene to p-chloro-aniline as an example.

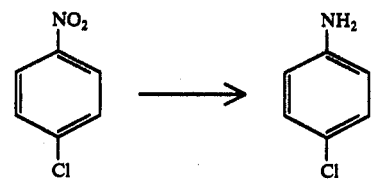

Suitable thio-esters for use as inhibitors in the process of the present invention are compounds of the formula

wherein
R¹ and R² are identical or different and represent optionally substituted alkyl or aryl radicals, it being possible for the radicals R¹ and R² optionally to be linked by a bond or a hetero atom to form a carbocyclic or heterocyclic ring, respectively and n represents 1 or 2.

Thio-ethers of the formula

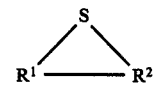

wherein
R¹ and R² have the abovementioned meaning, are particularly preferred for the process according to the invention.

Optionally substituted alkyl radicals (R¹ and R²) which may be mentioned are straight-chain or branched hydrocarbon radicals with up to 12, and preferably up to 6, carbon atoms. The following radicals may be mentioned as examples: methyl, ethyl, propyl, iso-propyl, butyl, iso-butyl, pentyl, iso-pentyl, hexyl, iso-hexyl, heptyl, iso-heptyl, octyl, iso-octyl, nonyl, iso-nonyl, decyl, iso-decyl, undecyl, iso-undecyl, dodecyl, iso-dodecyl, octadecyl and iso-octadecyl.

It is also possible for the optionally substituted alkyl radicals (R¹ and R²) to represent a cycloaliphatic hydrocarbon radical with 4 to 8, and preferably 5 to 6, carbon atoms. The following radicals may be mentioned as examples: cyclobutyl, cyclopentyl, cyclohexyl, cycloheptyl and cyclooctyl.

Optionally substituted aryl radicals (R¹ and R²) which may be mentioned are carbocyclic aromatic radicals with 6 to 12 carbon atoms, such as, for example, the phenyl, naphthyl and biphenyl radical, preferably the phenyl radical.

It is also possible for the alkyl radicals and aryl radicals (R¹ and R²) to be linked to form a carbocyclic or heterocyclic ring. Generally the ring has between 4 and 12 atoms therein.

Compounds of the formula

wherein R¹ and R² have the abovementioned meaning, may be mentioned as examples in which R¹ and R² are linked to form a carbocyclic ring.

Compounds of the formula

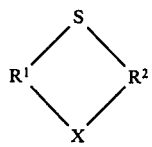
(III)

wherein
R[1] and R[2] have the abovementioned meaning and
X represents an oxygen, sulphur or nitrogen atom, may be mentioned as examples in which R[1] and R[2] are linked by a hetero atom to form a heterocyclic ring.

Substituents of the radicals R[1] and R[2] can be all the radicals which are not changed under the reaction conditions. The following substituents may be mentioned as examples: $C_1$-$C_6$-alkyl radicals, such as methyl, ethyl, propyl, isopropyl, butyl, iso-butyl, pentyl, iso-pentyl, hexyl and iso-hexyl, preferably methyl and ethyl, aryl radicals, such as phenyl, naphthyl and diphenyl, preferably phenyl, the hydroxyl group, the nitrile group, the carboxyl group, straight-chain or branched carboalkoxy radicals with up to 6 carbon atoms, such as carbomethoxy, carboethoxy, carbopropoxy, iso-carbopropoxy, carbobutoxy, iso-carbobutoxy, carbopentoxy, iso-carbopentoxy, carbohexoxy and iso-carbohexoxy, preferably carbomethoxy and carboethoxy, straight-chain or branched alkoxy radicals with up to 6 carbon atoms and cycloalkoxy radicals with 5 and 6 carbon atoms, such as methoxy, ethoxy, propoxy, iso-propoxy, butoxy, iso-butoxy, pentoxy, iso-pentoxy, hexoxy, iso-hexoxy, cyclopentoxy and cyclohexoxy, preferably methoxy and ethoxy, and aryloxy radicals, such as phenoxy, naphthoxy and phenylphenoxy, preferably phenoxy.

The preparation of the thio-ethers is in itself known (Ber. dtsch. chem. Ges. 19, 3259 (1886) and J. Chem. Soc. 119, 1255 (1921). The following thio-ethers may be mentioned as examples: bis-(2-hydroxyethyl) sulphide, bis-(2-hydroxyethyl) disulphide, bis-(2-hydroxypropyl) sulphide, bis-(2-hydroxypropyl) disulphide, thiodipropionic acid, sodium thiodipropionate, potassium thiodipropionate, thioanisole, thiodipropionic acid dimethyl ester, diphenyl sulphite, dithiane, thioxane, thiophene and benzthiazole.

Thio-ethers which are completely or partially soluble in water are preferably used for the process according to the invention. Bis-(2-hydroxy-ethyl) sulphide and thioxane are particularly preferentially employed.

The process according to the invention can advantageously be carried out in a weakly basic medium. The reaction is preferably carried out in a pH range of 7 to 9. The basic medium can be obtained, for example, by adding sodium bicarbonate, sodium carbonate, sodium hydrogen phosphate, calcium hydroxide or aliphatic amines, such as triethylamine or tetraethylenepentamine, and preferably sodium bicarbonate.

The amount of base which is added is 0.01 to 0.2% by weight, preferably 0.05 to 0.1% by weight, relative to the nitro compound employed.

Chlorinated aromatic nitro compounds which may be hydrogenated by the process of the present invention comprise compounds of the formula

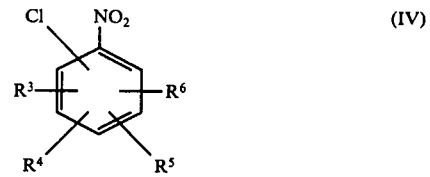
(IV)

wherein R[3], R[4], R[5] and R[6] are identical or different and represent hydrogen, halogen, nitro, hydroxyl, nitrile, carboxyl or an optionally substituted alkyl, aryl, aralkyl, alkoxy, aralkoxy or arylsulphone radical, may be mentioned as examples. Halogens can be fluorine, chlorine, bromine and iodine, preferably chlorine.

The scope of values for the radicals R[3], R[4], R[5] and R[6] when these are optionally substituted alkyl or aryl, corresponds to the scope of values for the radicals R[1] and R[2] in formula I.

The following halogenated aromatic nitro compounds may be mentioned as examples: o-chloro-nitrobenzene, m-chloro-nitrobenzene, p-chloro-nitrobenzene, 2,3-dichloro-nitrobenzene, 2,4-dichloro-nitrobenzene, 2,5-dichloro-nitobenzene, 3,4-dichloro-nitrobenzene, 2,3,5-trichloro-nitrobenzene, 2,4,5-trichloro-nitrobenzene, 3-chloro-4-nitrophenol, 2,3-dichloro-4-nitrophenol, 3-chloro-5-nitrophenol, 3-chloro-4-methoxy-nitrobenzene, 4-chloro-2-methoxy-nitrobenzene, 2-chloro-6-nitrohydro quinone dimethyl ether, nitro-4-chloro-diphenyl ether, 2-nitro-4,6-dichloro-diphenyl ether, 4,4'-dichloro-2-nitro-diphenyl ether, 4-chloro-3-nitrodiphenyl, 3-chloro-3'-nitro-diphenyl, 4-chloro-2-methyl-nitrobenzene, 3-chloro-5-tert.-butyl-nitrobenzene, 4-chloro-2-nitro-diphenylsulphone, 2-chloro-4-nitrobenzoic acid, 4-chloro-3-nitrobenzoic acid, 2,6-dichloro-3-nitrobenzoic acid, 4-chloro-2-nitrophenylacetic acid, and 3,4-dichloro-6-nitroaniline.

The process according to the invention can be carried out in the presence of a catalyst consisting of noble metals on charcoal.

Noble metals which may be mentioned are the elements of group eight of the periodic table (Mendelejev), such as ruthenium, rhodium, palladium, osmium, iridium and platinum, preferably palladium and platinum and particularly preferentially platinum.

The preparation of a catalyst comprising noble metal on charcoal, which is employed for the process according to the invention, can be carried out in a manner which is in itself known. For example, the charcoal is suspended in an aqueous solution of a noble metal compound and the noble metal is then precipitated onto the charcoal by adding a reducing agent, such as hydrogen or hydrazine.

There are no special requirements in respect of the nature of the charcoal. Charcoals which have an effective surface area (BET) of at least 800 m$^2$/g are preferred.

Noble metal-on-charcoal catalysts which contain 0.5 - 1% by weight of the noble metal are preferred. The amount of catalyst which is employed for carrying out the process according to the invention is not critical and can be varied within wide limits. In general, 0.02 - 3% by weight, and preferably 0.1 - 1% by weight, of the noble metal catalyst is used, relative to the nitro compound employed. The ratio by weight of the amount of sulphur thio-ether compounds to the amount of catalyst (noble metal and charcoal) is generally 0.001 - 0.125 : 1, preferably 0.0025 – 0.025 : 1 and particularly preferentially 0.005 – 0.0125 : 1.

The thio-ether inhibitors can be employed both in the pure form and as mixtures of different inhibitors. Advantageously, the thio-ether inhibitors are employed in the process according to the invention in the form of solutions. For example, they can be added to the reaction mixture as an approximately 0.1% strength by weight aqueous solution or 0.1% strength by weight solution in toluene.

It is also possible to mix the inhibitor with the catalyst prior to the reaction.

For the process according to the invention, the inhibitor is generally added only when the noble metal catalyst is used for the first time. Even after it has been repeatedly used several times, or in the case of a continuous procedure over a long period, the noble metal catalyst retains its activity and selectivity without fresh inhibitor being continuously added. If there is a gradual reduction in the selectivity, the selectivity can be restored to its former value by adding fresh inhibitor. When fresh inhibitor is added, about 1 to 10% by weight of the amount of the thio-ester initially employed is used.

The process according to the invention is usually carried out in solution. Solvents which can be used are all solvents which are inert under the reaction conditions. Suitable solvents which may be mentioned are water, methanol, isopropanol, toluene, benzene and xylene, preferably methanol and toluene. If they are liquid at the reaction temperature, the chlorinated aromatic amines expected as the end product can also be used as solvents.

The process according to the invention can, for example, be carried out as follows.

The starting material, the solvent, the catalyst, the sulphur compound and, optionally, the base are initially introduced into an autoclave. After closing the autoclave, the air is driven out with nitrogen and the nitrogen is then driven out with hydrogen.

The contents of the autoclave are heated up to the reaction temperature and the hydrogen is then passed in.

The process according to the invention is generally carried out at a temperature of 30° to 200° C, preferably of 60° to 120° C and particularly preferentially of 80° to 110° C.

The hydrogen is passed into the reaction mixture as a gas. In general, the reaction is carried out under hydrogen pressures of 5 to 150 atmospheres gauge and preferably of 10 to 30 atmospheres gauge.

When the reaction has ended, the catalyst is separated off by filtering. The chlorinated aromatic amines can then be obtained from the filtrate, for example by distillation.

The process according to the invention can be carried out both discontinuously and continuously.

The advantage of the process according to the invention is that it is possible, by means of simple addition of an inhibitor to the reaction mixture, to hydrogenate aromatic chloronitro compounds, with high selectivity, to the corresponding aromatic chloroamino compounds. The inhibitors used are toxicologically acceptable and are employed only in extremely small amounts.

The process according to the invention is advantageously distinguished by a good reproducibility and makes it possible for the catalysts which are employed to be re-used many times.

Aromatic chloronitro compounds are intermediate products for dyestuffs (U.S. Patent Specifications 2,439,798, 2,373,700, 2,470,094 and 3,125,402; German Auslegeschrift (German Published Specification) 1,069,114; German Offenlegungsschrift (German Published Specification) 2,232,524 and French Patent Specification 648,068) and plant protection agents (German Auslegeschrift (German Published Specification), 1,108,977, German Auslegeschrift (German Published Specification) 1,188,861 and German Auslegeschrift (German Published Specification) 1,905,598).

EXAMPLES

General Procedure

The aromatic nitrochloro compound, the solvent, the catalyst and the sulphur compound, which is optionally dissolved in water or in an organic solvent, are initially introduced into an autoclave.

(In order to ensure that the medium is basic during the entire reaction, a base can optionally be added.)

The autoclave is flushed, first with nitrogen and then with hydrogen. The reaction mixture is then heated to the temperature indicated in the Examples which follow and the hydrogenation is carried out under the hydrogen pressure indicated in the Examples until no further hydrogen is taken up.

When the reaction has ended, the catalyst is filtered off and can then be made available direct for further hydrogenations. The aromatic aminochloro compound is isolated from the filtrate by customary methods (for example by distillation).

The Examples which follow are carried out in accordance with the general instructions:

EXAMPLE NO. 1 TO 4

Hydrogenation of 100 g of o-chloronitrobenzene in 300 ml of toluene over 4 g of a 1% strength platinum-on-charcoal catalyst (surface area: ~ 800 m$^2$/g) under the influence of various inhibitors.

Reaction temperature: 100° C
H$_2$ pressure: 10 atmospheres

| Example No. | Inhibitor | Reaction time | Aniline content | o-Chloroaniline content |
|---|---|---|---|---|
| 1 | 0.02 g of bis-(2-hydroxyethyl) sulphide | 63 minutes | 0.026% | 99.974% |
| 2 | 0.15 g of thioxane | 59 minutes | 0.016% | 99.982% |
| 3 | 0.05 g of thiophene | 42 minutes | 0.066% | 99.932% |
| 4 | 0.01 g of dithiane | 140 minutes | 0.044% | 99.720% |

EXAMPLE 5 TO 7

Hydrogenation of o-nitrochlorobenzene in approximately three times the amount of toluene as a function of the amount of catalyst:

| catalyst: | 1% strength platinum-on-charcoal contact catalyst (surface area about 800 m²/g) |
|---|---|
| inhibitor: | bis-(2-hydroxyethyl) sulphide |
| reaction temperature: | 100° C |
| H₂ pressure: | 10 atmospheres |

| Example No. | Amount of catalyst | Amount of o-nitrochloro- benzene and of inhibitor | Reaction time | Aniline content | o-Chloro- aniline content |
|---|---|---|---|---|---|
| 5 | 10 kg | 4,000 kg; 50 g | 17 hours | 0.043% | 99.957% |
| 6 | 0.4 g | 0.1 kg; 0.005 g | 120 minutes | 0.076% | 99.415% |
| 7 | 2 g | 0.1 kg; 0.01 g | 53 minutes | 0.051% | 99.949% |
| 1 | 4 g | 0.1 kg; 0.02 g | 63 minutes | 0.026% | 99.974% |

EXAMPLE 8

Hydrogenation of 100 g of o-nitrochlorobenzene in 300 ml of toluene over 4 g of a 1% strength platinum-on-charcoal contact catalyst.

| A: charcoal with a surface area of ~800 m²/g |  |
|---|---|
| B: charcoal with a surface area of ~2,000 m²/g |  |
| inhibitor: | 0.02 g of bis-(2-hydroxyethyl) sulphide |
| reaction temperature: | 100° C |
| H₂ pressure: | 10 atmospheres |

|  | Reaction time | Aniline content | o-Chloroaniline content |
|---|---|---|---|
| A | 78 minutes | 0% | 100% |
| B | 49 minutes | 0% | 100% |

EXAMPLE 9 TO 13

Hydrogenation of 100 g of o-nitrochlorobenzene in 300 ml of toluene over 4 g of a 1% strength platinum-on-charcoal catalyst (surface area ~ 800 m²/g) as a function of the amount of inhibitor and the H₂ pressure. Inhibitor: bis-(2-hydroxy-ethyl) sulphide reaction temperature: 100° C.

| Example No. | Amount of inhibitor | H₂ pressure | Reaction time | Aniline content | o-Chloroaniline content |
|---|---|---|---|---|---|
| 9 | 0.005 g | 10 atmospheres | 56 minutes | 0.052% | 99.727% |
| 10 | 0.04 g | 10 atmospheres | 163 minutes | 0.020% | 99.731% |
| 11 | 0.05 g | 10 atmospheres | >180 minutes | not completely hydrogenated | |
| 12 | 0.05 g | 100 atmospheres | 25 minutes | — | 99.85 % |
| 13 | 0.10 g | 100 atmospheres | 36 minutes | — | 99.876% |

EXAMPLE 14

Hydrogenation of 100 g of o-chloronitrobenzene in 300 ml of toluene over 4 g of a platinum-on-charcoal catalyst (surface area ~ 800 m²/g) with the addition of 0.01 g of bis-(2-hydroxyethyl) sulphide as the inhibitor.

| A: without the addition of a base |  |
|---|---|
| B: with the addition of 0.25 g of NaHCO₃ |  |
| reaction temperature: | 100° C |
| H₂ pressure: | 10 atmospheres |

| Aniline content | o-Chloroaniline content | pH value of the water of reaction | Reaction time | Iron dissolved from the V4A autoclave |
|---|---|---|---|---|
| A 0% | 100% | 5 | 88 minutes | 0.002 g |
| B 0.025% | 99.975% | 9.2 | 85 minutes | 0.0006 g |

As a comparison of Experiment A and Experiment B shows, it is possible, even when the elimination of chlorine does not take place, to reduce the corrosive attack on ferrous apparatuses even further when the medium is kept basic.

EXAMPLE 15 TO 23

Hydrogenation of p-nitrochlorbenzene in 300 ml of toluene over a 1% strength platinum-on-charcoal catalyst (surface area ~ 800 m²/g), repeated several times.

| Inhibitor: | bis-(2-hydroxyethyl) sulphide dissolved in 10 ml of water |
|---|---|
| Base added: | 0.25 g of NaHCO₃ per charge |
| Reaction temperature: | 100° C |
| H₂ pressure: | 10 atmospheres |

| Example No. | Amount of catalyst | Feed of p-nitro- chlorobenzene | Amount of inhibitor | Reaction time | Aniline content | p-Chloroaniline content |
|---|---|---|---|---|---|---|
| 15 | 4 g Contact catalyst from: | 100 g | 0.02 g | 66 minutes | — | 100% |
| 16 | Example 15 | " | — | 51 minutes | — | 100% |
| 17 | Example 16 | " | — | 73 minutes | — | 100% |
| 18 | Example 17 | " | — | 54 minutes | — | 100% |

-continued

| Example No. | Amount of catalyst | Feed of p-nitro-chlorobenzene | Amount of inhibitor | Reaction time | Aniline content | p-Chloroaniline content |
|---|---|---|---|---|---|---|
| 19 | Example 18 | " | — | 38 minutes | 0.021% | 99.822% |
| 20 | Example 19 | " | — | 38 minutes | 0.044% | 99.953% |
| 21 | Example 20 | " | — | 30 minutes | 0.045% | 99.955% |
| 22 | Example 21 | " | — | 34 minutes | 0.047% | 99.950% |
| 23 | Example 22 | " | — | 49 minutes | 0.035% | 99.807% |

The pH value of the water of reaction is about 9 in each case. The contact catalyst, which was used nine times, has an unchanged activity and can be used for further hydrogenations.

EXAMPLE 24

Analogously to Example No. 15 to 23, the same contact catalyst is used 35 times in succession for the hydrogenation of m-nitrochlorbenzene without its activity or selectivity being decreased. In this example, as a rule, a further 10% of the amount of bis-(2-hydroxyethyl) sulphide originally added are added after every second charge. The reaction conditions correspond to those for the hydrogenation of o-nitrochlorobenzene and p-nitrochlorobenzene.

| Charge No. | Aniline content | m-Chloroaniline content |
|---|---|---|
| 1 to 35 | 0.029% | 99.970% |
|  | 0.128% | 99.800% |

EXAMPLE 25

Hydrogenation of 2,5-dichloronitrobenzene.

100 g of 2,5-dichloronitrobenzene are dissolved in 300 ml of toluene and hydrogenated over 4 g of a 1% strength platinum-on-charcoal contact catalyst (surface area about 2,000 m²/g) at 100° C and under a hydrogen pressure of 10 atmospheres. 0.005 g of bis-(2-hydroxyethal) sulphide is employed as the inhibitor.

The reaction has ended after 34 minutes; after distilling off the toluene, 2,5-dichloroaniline (purity 100%) is obtained in 98% yield after fractional distillation.

EXAMPLE 26

Preparation of 4-chloro-3-aminobenzoic acid.

55.1 g of 4-chloro-3-nitrobenzoic acid are hydrogenated, in accordance with the general instructions, at 100° C and under a H₂ pressure of 10 atmospheres, in 350 ml of methanol and according to A: over 4 g of a 1% strength platinum-on-charcoal contact catalyst (surface area ~ 800 m²/g), with the addition of 0.18 g of bis-(2-hydroxyethyl) sulphide dissolved in 10 ml of water, for about 20 minutes and according to B: over 4 g of a 1% strength palladium-on-charcoal contact catalyst (surface area ~ 2,000 m²/g), with the addition of 1.18 g of bis-(2-hydroxyethyl) sulphide dissolved in 10 ml of water, for about 40 minutes.

When the reaction has ended, the contact catalyst is filtered off at about 60° C and the filtrate is concentrated by distilling off about 220 ml of methanol. About 320 ml of water are added to the resulting crystal slurry, which can be stirred easily, the mixture is cooled to about 15°–20° C and the product is then filtered off.

4-Chloro-3-aminobenzoic acid is obtained according to A: in a yield of 92% of theory
  melting point: 215° C
  content of 3-aminobenzoic acid: 0.05%
and according to B: in a yield of 88.2% of theory
  melting point: 215/216° C
  content of 3-aminobenzoic acid: about 0.1%

What is claimed is:

1. In a process for the preparation of the chlorinated aromatic amine by a hydrogenation of the corresponding chlorinated nitro-aromatic compound in the presence of a noble metal catalyst on a carbon support and in the co-presence of a sulfur compound, the improvement in that the sulfur compound is a thio-ether.

2. A process according to claim 1 wherein the thioether has the formula

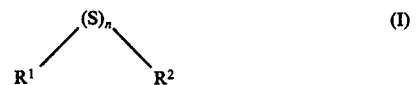

wherein
  R¹ and R² are identical or different and represent optionally substituted alkyl or aryl radicals or R¹ and R² are taken together to form a carbocyclic or heterocyclic ring, and
  n represents 1 or 2.

3. A process according to claim 2 wherein the thioether of the formula

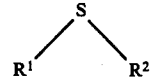

is employed wherein
  R¹ and R² have the previously assigned significance.

4. A process according to claim 1 wherein the thioether employed is bis-(2-hydroxyethyl) sulfide.

5. A process according to claim 1 wherein the thioether employed is thioxane.

6. A process according to claim 1 wherein the reaction is carried out in the pH range of 7 to 9.

7. A process according to claim 1 wherein the noble metal catalyst is present in the reaction mixture in an amount of 0.02–3% by weight.

8. A process according to claim 7 wherein the weight ratio of the sulfur compound to the amount of catalyst is in the range of 0.001–0.125:1.

9. A process according to claim 8 wherein the weight ratio of the amount of sulfur compound to the amount of catalyst is in the range of 0.0025–0.025:1.

10. A process according to claim 9 wherein the weight ratio of the amount of sulfur compound to the amount of catalyst is in the range of 0.005–0.0125:1.

11. A process according to claim 2 wherein R¹ and/or R² is substituted and the substituent is a C₁-C₆ alkyl, hydroxyl, nitrile, phenyl, naphthyl, biphenyl, carboxyl, C₁-C₆ carboalkoxy, C₁-C₆ alkoxy or C₅-C₆ cycloalkoxy radical.

12. A process according to claim 1 wherein the reaction is conducted at a temperature of 30°–200° C.

13. A process according to claim 12 wherein the reaction is conducted at a hydrogen pressure of 5 to 150 atmospheres gauge.

* * * * *